Figure 1:
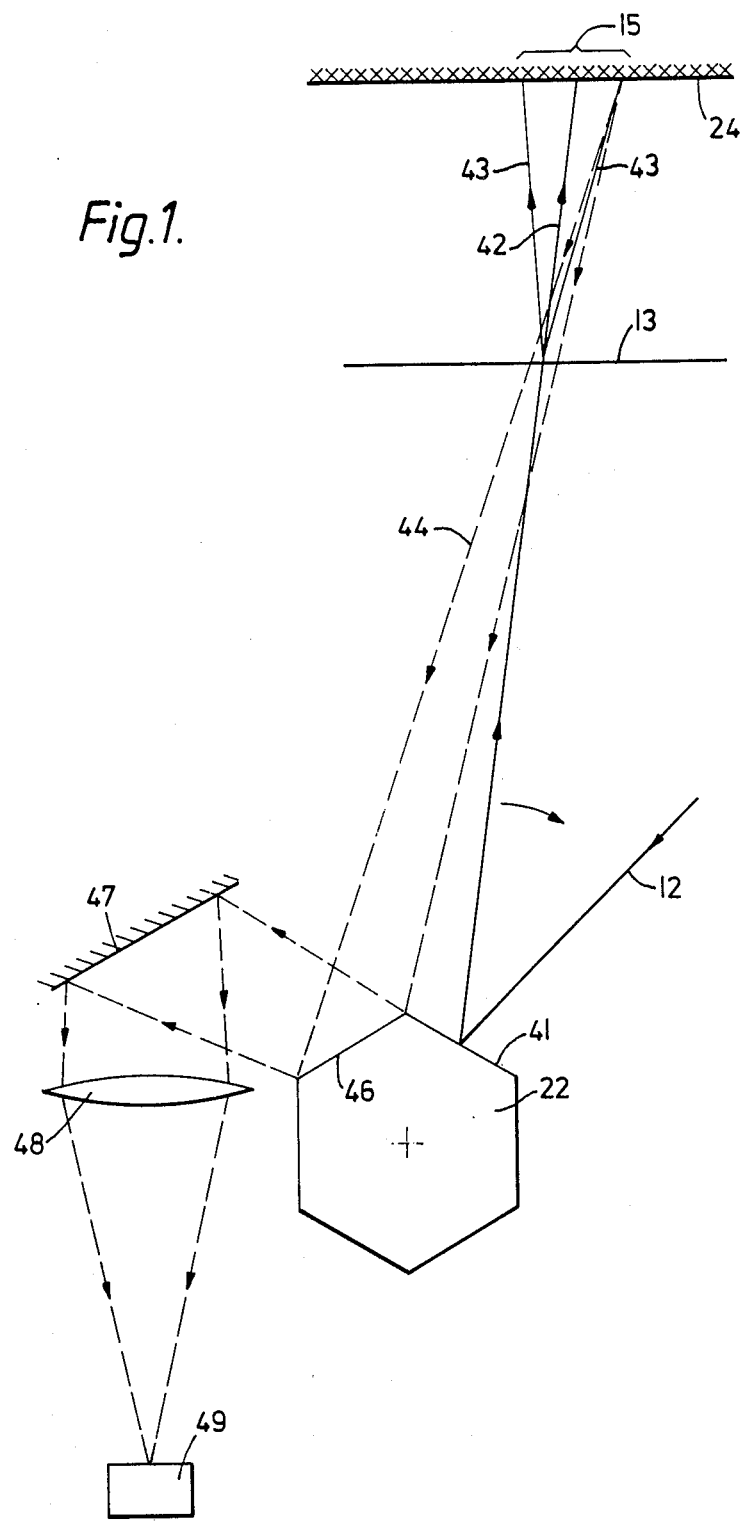

United States Patent [19]

West

[11] Patent Number: 4,797,558

[45] Date of Patent: Jan. 10, 1989

[54] INSPECTION APPARATUS INCLUDING PHOTODETECTION AND SCANNING APPARATUS

[75] Inventor: Robert N. West, Chislehurst, England

[73] Assignee: Sira Limited, Chislehurst, England

[21] Appl. No.: 43,654

[22] Filed: Apr. 28, 1987

[30] Foreign Application Priority Data

Apr. 28, 1986 [GB] United Kingdom ................. 8610305

[51] Int. Cl.⁴ .......................... G01N 21/88; H01J 3/14
[52] U.S. Cl. .................................... 250/572; 250/235; 250/236; 350/6.8
[58] Field of Search ................................ 250/234–236, 250/563, 572; 350/6.7, 6.8; 356/431, 444

[56] References Cited

U.S. PATENT DOCUMENTS

| 4,018,504 | 4/1977 | Wu et al. | 350/6.8 |
| 4,170,398 | 10/1979 | Koester | 350/6.8 |
| 4,523,093 | 6/1985 | Neumann | 250/234 |

Primary Examiner—David C. Nelms
Assistant Examiner—Stephone B. Allen
Attorney, Agent, or Firm—Sughrue, Mion, Zinn, Macpeak and Seas

[57] ABSTRACT

An inspection apparatus for inspecting, for example, sheet material, in which a beam of radiation 12 is scanned across a sheet 13 by means of a first facet 41 of a rotating mirror drum 22. Scattered radiation from the sheet is received by a second facet 46 and 2 is passed to a photodetector 49 for analysis.

8 Claims, 2 Drawing Sheets

INSPECTION APPARATUS INCLUDING PHOTODETECTION AND SCANNING APPARATUS

The present invention relates to inspection apparatus.

In particular, the apparatus, in general terms, refers to an apparatus of a similar type to our earlier European patent application No. 182471 and our previous UK Patent No. 2054835.

The apparatus may be of a type for inspecting an object, for example for inspecting its surface or, if the object is transparent to the radiation used in the inspection, for inspecting the bulk of the object. Preferred arrangements for the apparatus are particularly applicable to the inspection of sheet material.

Our earlier European patent application No. 182471 shows an inspection apparatus for inspecting, for example, sheet material in which a beam of radiation is scanned across a sheet by means of a rotating mirror drum 22, radiation from the sheet 13 being influenced by the sheet 13 and thereafter being passed to a retroreflective screen 24; the image 15 on the retroreflective screen 24 is inspected by bringing the reflected light back to a focus 25, on a target 33 via the same facet of the mirror drum 22 so that the conjugate image 25 is stationary (ie is descanned) and may be viewed by a photodetector 27.

The present invention provides inspection apparatus comprising a radiation source, a multiple mirror scanner, and a radiation detector means in which, in use a beam of radiation is scanned across an object by reflection from a facet of the multiple mirror scanner and radiation influenced by the object passed back to the multiple mirror scanner and reflected by another facet to the radiation detector means.

Although we refer throughout to "light" and "optical" it will be understood that this invention can be used with radiation of other wavelengths, for example, infrared and ultra violet. Indeed, in examining some materials such as light sensitive sheets it is essential to use wavelengths to which the light sensitive sheets are not sensitive.

Figure 2:
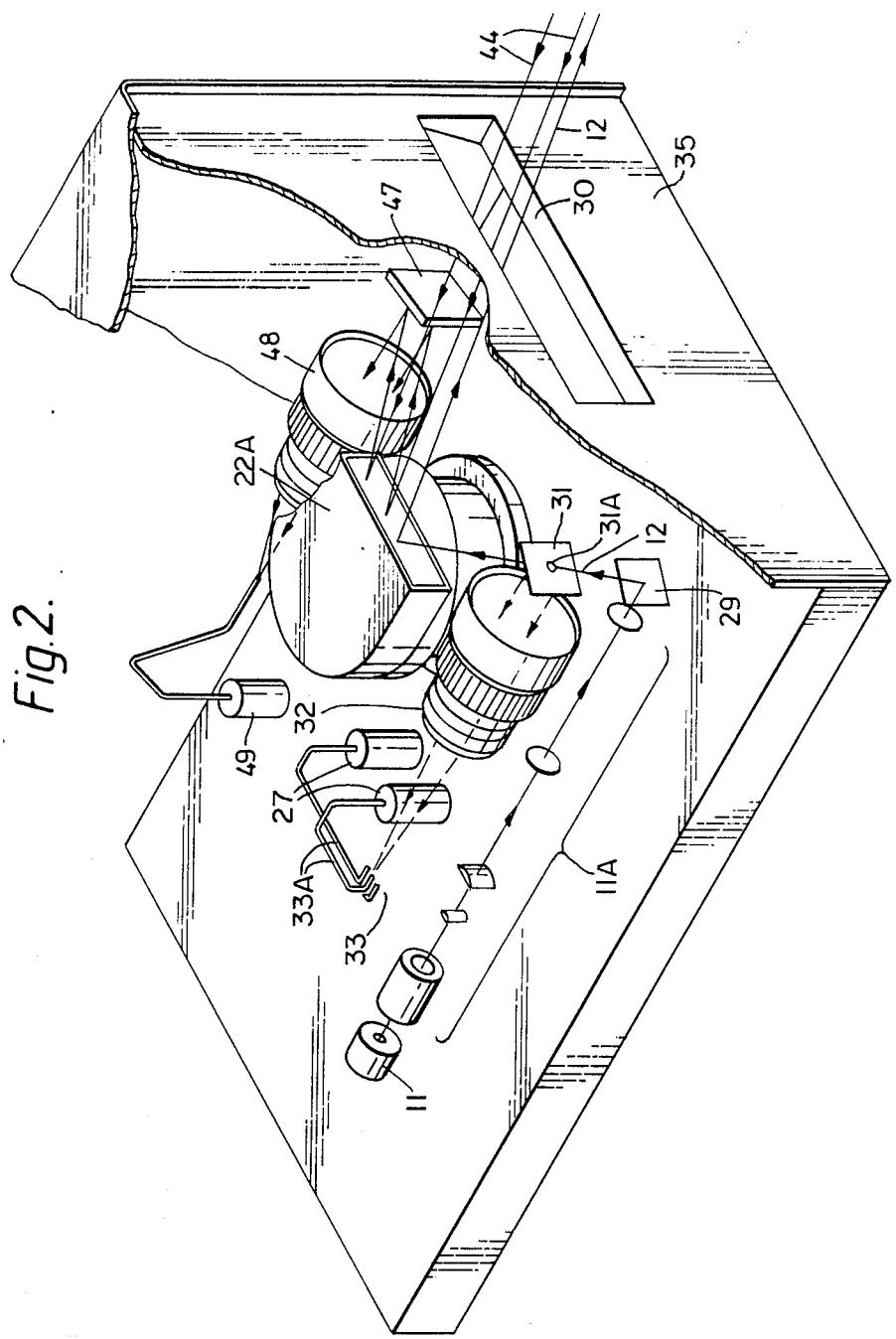

The invention will be described by way of example only and with reference to the accompanying drawings in which FIG. 1 shows, in diagramatic form, part of the optical arrangement of the apparatus according to the invention, and, FIG. 2 shows a perspective view partly cut away, of a preferred embodiment of the invention.

Various parts are given the same reference numerals as corresponding parts in our earlier European patent application No. 182471 and the figures of that earlier patent application are herein incorporated in this specification.

Referring to FIG. 1 of the accompanying drawings, an incident light beam 12 strikes a facet 41 of a rotating polygonal mirror drum 22 and passes to a sheet 13 across which it is scanned by rotation of the mirror drum 22. The light then passes to a retroreflective screen 24 where an image 15 is formed, although it will be understood that the image 15 is not necessarily in focus. The image 15 is focussed back onto target 33 via the facet 41 of the mirror drum 22.

Let us consider the particular circumstances whereby there is a flaw in the sheet 13 which causes the beam to scatter and so instead of there being a small defined spot 15 on the sheet 24, the beam 12 forms a central spot together with a larger area of scattered light. In the drawing, the central beam path which forms the central spot is indicated at 42 whereas the peripheral beam path which forms the surrounding zone of scattered light is indicated at 43. If the fault in the sheet 13 is such as to effectively eliminate the bright central spot then the conjugate image 25 formed via the facet 41 will be easily analysed as the output signal from the two parts of the detector 36, 37 will be of the same order of magnitude.

However, it is common for the central spot created by the central beam 42 to be very much brighter than the surrounding scattered light surface area and this effect is emphasised by the use of retroreflective material in screen 24. Retroreflective material returns an incident beam of light along the same beam path, but with a small cone angle. The cone angle may be as low as one degree. Now as is clear from the accompanying drawing, most of the light from the central beam 42 will be returned to the facet 41, but scattered light, at, say the periphery of beam path 43 will tend to be returned in a cone illustrated by the dotted lines 44. Thus a substantial proportion of the scattered light at the periphery of the scattered light area will not be returned to the facet 41 and so the relative light signal received by the two photodetector portions 36, 37 will be disproportionate, that received by 37 being very much less than that received by 36. In normal operation, therefore, it is likely that the signal from the scattered light detector may well be swamped by the cental cone, since the scattered light signal will be disproportionately smaller than the central light signal.

We, therefore, propose that in addition to viewing the image on the surface 24 via the same facet 41 as the incident beam 12 there is provided an optical system for collecting light returning from the image 15 on the surface 24 via at least one adjacent facet, for example, facet 46. It will be clear that the light returning to facet 46 will, in this case, contain a proportionately increased amount of scattered light compared with the central beam 42 and in circumstances where we wish to consider the scattered light in more detail this is a preferred arrangement. The optical system to collect the light reflected back to the facet 46 comprises a plane mirror 47 an imaging lens 48 and a photodetector 49 which may be of the general type similar to the photo detector 33.

In this way the relative ratio between the signals received by the two parts 36, 37 of the photo detector 49 will proportionately favour the scattered light and, therefore, the signal relating to scattered light will be proportionately larger than the signal for the central beam.

FIG. 2 illustrates in more detail a preferred embodiment of apparatus according to the invention. Apparatus is mounted within a closed cabinet 35 the front face of which includes a slot 30. The cabinet 35 mounts therein a laser 11, and beam shaping optical components 11A for producing the beam 12. The beam 12 is reflected from a mirror 29 and is passed to a beam splitter 31 in the form of a mirror having a central aperture 31A through which the beam 12 passes. The beam 12 is passed to the mirror drum scanner 22 which is mounted inside a hood 22A, the mirror drum scanner 22 rotating and scanning the beam 12 through the slot 30 across the object 13 under inspection. Some of the returning light passes back to the facet 41 which has reflected the outgoing beam 12 and this is received by the mirror 31 and reflected to components 32,27,33,33A in a manner described in our European Patent Application No. 182471.

The scattered light is, as with FIG. 1, indicated as returning along the lines 44 and passes to an adjacent facet 46 of the mirror drum 22 and is reflected to the mirror 47 and via the imaging lens 48 onto the photodetector 49. The operation of this part of the apparatus is as described with reference to FIG. 1.

The invention is not restricted to the details of the foregoing example.

I claim:

1. Inspection apparatus comprising:
   a radiation source;
   a rotatable mirror scanner having a plurality of facets so that, as the mirror scanner rotates, it scans a beam of radiation from the radiation source across an object to be inspected by reflection from a suitably disposed facet of the mirror scanner; and
   a plurality of radiation detector means, one of the radiation detector means receiving the central part of the beam of radiation, after it has been influenced by the object, via said suitably disposed facet of the mirror scanner, and another of the radiation detector means being positioned to receive radation scattered by the object and reflected by another facet of the mirror scanner.

2. Apparatus as claimed in claim 1 further including retroreflective material positioned so that the beam of radiation after scanning across said object is intercepted by said retroreflector material and retrorefracted back to the object and back to the mirror scanner.

3. Inspection apparatus for inspecting an object, comprising:
   a laser for outputting a beam;
   beam shaping means for shaping said beam from said laser;
   a mirror scanner having a plurality of facets, the mirror scanner being rotable about an axis;
   a plurality of optical focusing means; and
   a plurality of photodetector means, wherein the beam shaping means is passed to a suitably disposed facet of the mirror scanner and rotation of said mirror scanner causes said facet to scan said beam across an object to be inspected, radiation influenced by the object and forming a central part of the returning beam being passed back from the object to the mirror scanner and being reflected by said suitably disposed facet to a first one of the plurality of optical focusing means and thence to a first one of the plurality of photodetector means, and radiation scattered by the object being passed back from the object to the mirror scanner and reflected by another facet of said mirror scanner to a second one of the plurality of optical focusing means and thence to a second one of the plurality of photodetector means.

4. Inspection apparatus comprising:
   a radiation source;
   a mirror scanner having a plurality of facets for scanning a beam of radiation from the radiation source across an object to be inspected by reflection from a suitably disposed facet of the mirror scanner;
   retroreflector means positioned to receive radiation influenced by the object and to reflect said radiation back to the object so that the radiation is influenced again by the object, said radiation which has been twice influenced by the object being returned to the mirror scanner and being reflected by another facet; and
   first radiation detector means positioned to receive radiation reflected by said another facet.

5. Apparatus as claimed in claim 4, further comprising second radiation detector means for receiving radiation influenced by the object, passed to the retroreflector, reflected from the retroreflector, and influenced again by the object, and reflected by said suitably disposed facet of the mirror scanner.

6. Apparatus as claimed in claim 5, further comprising second optical focusing means and second photodetector means, said second optical focusing means and said second photodetector means receiving radiation from the object reflected by said suitably disposed facet.

7. Inspection apparatus for inspecting an object, comprising:
   a laser;
   beam shaping means for shaping a beam from said laser and outputting a shaped beam;
   a mirror scanner having a plurality of facets, the mirror scanner being rotatable about an axis;
   first optical focusing means;
   first photodetector means;
   wherein the shaped beam is passed to a suitably disposed facet of the mirror scanner and rotation of said mirror scanner causes said facets successively to scan the beam across an object to be inspected; and
   retroreflector means positioned to receive radiation influenced by the object, said retroreflector means reflecting the radiation back to the object and thence back to the mirror scanner, reflected radiation being reflected by another facet of the mirror scanner to the optical focusing means and thence to the first photodetector means.

8. Apparatus as claimed in claim 7, further comprising second optical focusing means and second photodetector means, said second optical focusing means and second photodetector means receiving radiation from the object reflected by said suitably disposed facet.

* * * * *